United States Patent [19]
Tarantino

[11] Patent Number: 5,863,549
[45] Date of Patent: Jan. 26, 1999

[54] METHODS FOR THE SUSTAINED RELEASE OF BIOLOGICALLY ACTIVE COMPOUNDS

[75] Inventor: Ralph Tarantino, Middletown, N.J.

[73] Assignee: Hoffmann-La Roche Inc., Nutley, N.J.

[21] Appl. No.: 701,274

[22] Filed: Aug. 22, 1996

Related U.S. Application Data

[62] Division of Ser. No. 154,679, Nov. 19, 1993, abandoned, which is a continuation of Ser. No. 960,752, Oct. 14, 1992, abandoned.

[51] Int. Cl.$^6$ .......................... B01J 13/00; A61K 31/685
[52] U.S. Cl. ...................... 424/422; 252/315.1; 514/944; 514/78
[58] Field of Search .................. 424/422; 252/315.1, 252/315.4; 514/944, 78

[56] References Cited

U.S. PATENT DOCUMENTS

| | | | |
|---|---|---|---|
| 4,252,793 | 2/1981 | Altman . | |
| 4,297,353 | 10/1981 | Maulding . | |
| 4,377,567 | 3/1983 | Geho . | |
| 4,578,391 | 3/1986 | Kawata et al. . | |
| 4,761,288 | 8/1988 | Mezei . | |
| 4,863,740 | 9/1989 | Kissel et al. . | |
| 4,910,224 | 3/1990 | Habib et al. . | |
| 5,035,895 | 7/1991 | Shibusawa et al. | 424/450 |
| 5,084,269 | 1/1992 | Kullenberg . | |
| 5,124,151 | 6/1992 | Viegas et al. . | |
| 5,143,731 | 9/1992 | Viegas et al. . | |
| 5,505,877 | 4/1996 | Krivohlavek | 252/314 |
| 5,660,854 | 8/1997 | Haynes et al. | 424/450 |
| 5,707,641 | 1/1998 | Gertner et al. | 424/422 |

FOREIGN PATENT DOCUMENTS

| | | |
|---|---|---|
| 21519864 | 7/1983 | France . |
| WO88/04556 | 6/1988 | WIPO . |
| WO89/00077 | 1/1989 | WIPO . |

OTHER PUBLICATIONS

Willimann et al., Journal of Pharmaceutical Sciences, vol. 81, No. 9, pp. 871–874 (1992).
Scartazzini et al., J. Phys. Chem., 92:829–833 (1988).
Kim, Pharmacy International., pp. 90–91 (Apr. 1983).
Luisi et al., Colloid & Polymer Science, 268:356–374 (1990).
Gennaro, A. R., Remington's Pharmaceutical Sciences, 17th Edition, pp. 403–404 (1985).
Ansel et al., "Pharmaceutical Dosage Forms and Drug Delivery Systems" 5th Ed., Lea & Fibiger Publishers, pp. 255, 259–261 (1990).

*Primary Examiner*—Robert H. Harrison
*Attorney, Agent, or Firm*—George W. Johnston; Dennis P. Tramalomi; Bruce A. Pokras

[57] ABSTRACT

The present invention is directed to a method for making in vivo a lecithin gel which provides for the sustained release of a biologically active compound contained in the gel. The present invention is also directed to a method for the sustained treatment of a human or other mammal with a therapeutic amount of a biologically active compound using the gel for the sustained release of the biologically active compound.

28 Claims, 6 Drawing Sheets

METHODS FOR THE SUSTAINED RELEASE OF BIOLOGICALLY ACTIVE COMPOUNDS

This is a division of application Ser. No. 08/154,679, filed Nov. 19, 1993, now abandoned, which is a Continuation of Ser. No. 07/960,752, filed Oct. 14, 1992, now abandoned.

BACKGROUND OF THE INVENTION

Sustained release dosage forms can decrease the frequency of administration of biologically active compounds and can also serve to reduce side effects by reducing peak serum levels of the compounds. There is also a significant advantage in administering biologically active proteins and polypeptides in sustained release dosage forms, since compounds of those classes generally have short biological half-lives.

Aqueous gels of pharmaceutically acceptable polymers such as gelatin, methylcellulose and polyethylene glycol have been used to control the release rate of drugs from dosage forms. The diffusion of drugs through such gels is hindered by the viscosity of these systems as well as the tortuous diffusion path that results from the three dimensional polymeric network that is present. These gels cannot easily be used to sustain the release of drugs administered parenterally due to the inherent problem of injecting such viscous materials through a hypodermic needle. In addition, the high molecular weight of these polymers prevent their rapid elimination from the injection site.

Lecithin gels are known per se, see e.g., Scartazzini et al., *J. Phys. Chem.*, 92:829–833 (1988) and Luisi et al., *Colloid Polym. Sci.*, 268:356–374 (1990). These gels are formed ex vivo by the addition of a critical amount of water to a mixture of lecithin and an organic solvent for the lecithin. Lecithin gels have many of the rheological properties of polymeric gels.

SUMMARY OF THE INVENTION

The present invention comprises injectable compositions for the sustained release of biologically active proteins and polypeptides wherein said compositions comprise lecithin, a lecithin solvent which is pharmaceutically acceptable for intramuscular or subcutaneous injection and which is not substantially soluble in water, and a biologically active compound.

The invention also comprises a method for the sustained treatment of a human or other mammal with a therapeutic amount of a biologically active compound which comprises the intramuscular or subcutaneous administration of a composition of the invention.

The invention also comprises a method of making in vivo a lecithin gel which provides the sustained release of a biologically active compound which comprises the intramuscular or subcutaneous injection of a composition of the invention.

DETAILED DESCRIPTION OF THE INVENTION

Figure 1:
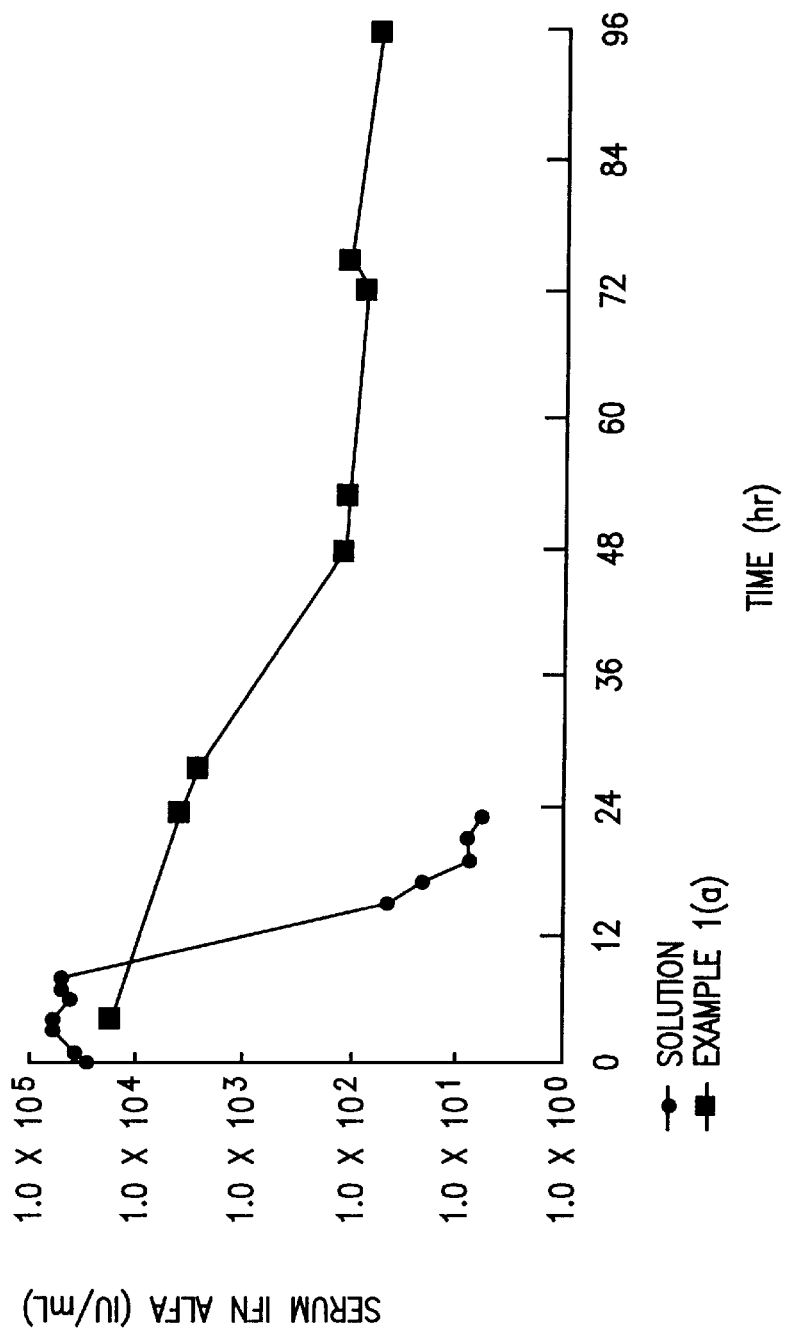
FIGS. 1 and 2 show the serum levels over time of interferon alfa-2a obtained from the administration in rats of interferon alfa-2a in conventional solutions and in compositions of the invention which contain no release-modifying excipients.

In accordance with the invention, it has been found that a lecithin gel can be formed in vivo by the intramuscular or subcutaneous injection of a solution of lecithin in an organic solvent. The lecithin gels of the invention are formed in vivo by absorption of water from the aqueous interstitial fluid at the injection site.

It has further been discovered that in vivo formed lecithin gels may be used as vehicles to sustain the in vivo release of biologically active compounds. The preferred compounds are proteins and polypeptides, e.g., interferon alfa (IFN alfa) and human growth hormone releasing factor (GRF) or analogs thereof having GRF activity.

The present invention comprises an injectable pharmaceutical composition which forms a lecithin gel in vivo for the sustained release of a biologically active compound comprising:

1) a pharmaceutically acceptable organic solvent which is not substantially soluble in water and which is capable of dispersing a lecithin and forming a lecithin gel upon the absorption of body fluids;

2) a therapeutically effective amount of said biologically active compound which is dispersed in said solvent; and 3) a lecithin which is dispersed in said solvent in an amount sufficient to cause gelation upon the absorption of body fluids.

The invention also comprises a method for the sustained treatment of a human or other mammal with a therapeutic amount of a biologically active compound which comprises the intramuscular or subcutaneous administration of a composition of the invention.

The invention also comprises a method of making in vivo a lecithin gel which provides the sustained release of a biologically active compound which comprises the intramuscular or subcutaneous injection of a composition of the invention.

As used herein, the term "lecithin" encompasses a complex mixture of acetone-insoluble, i.e., polar, phosphatides which consists chiefly of phosphatidyl choline, phosphatidyl ethanolamine, phosphatidyl serine, and phosphpatidyl inositol, combined with various amounts of other substances such as triglycerides, fatty acids, and carbohydrates, wherein the acetone-insoluble matter is not less than 50%. See, *The United States Pharmacopeia* (1990), p. 1942. The term "lecithin" also includes compositions which contain substantial amounts of one of the above-described phosphatides.

The source and particular composition of the lecithin is not critical so long as the lecithin is capable of forming a gel and is suitable for injection into humans or other mammals. Sources of lecithin include vegetable sources such as soybeans, corn, peanuts, and sunflower seeds. Examples of animal sources of lecithin are egg yolks and animal brain matter.

The preferred lecithin is derived from soy beans and contains a substantial per centage of phosphatidyl choline. Such a lecithin may be prepared from unpurified commercial soya lecithin (e.g., Type IV-S, Sigma Chemical Co., St. Louis, Mo.) by, for example, the method of Scartazzini et al., supra. Alternatively, purified soya lecithin containing >90% phosphatidyl choline is available commercially (e.g., LIPOID S 100, Lipoid KG, Frigenstr. 4, D-6700 Ludwigshafen 24, Germany; Type III-S, Sigma Chemical, supra).

Any organic solvent which is suitable for injection and in which lecithin, the biologically active compound, and any optional ingredients described below are dispersible may be used as the solvent for preparing the compositions of the invention, so long as the solvent is not substantially soluble in water and is capable of forming a lecithin gel upon the addition of the critical amount of water. As used herein, such substances are "dispersed" if they form either a true solution in the solvent or a stable suspension. The capability of a solvent to be useful in practicing the claimed invention may be determined in vitro by its ability to form a lecithin gel through the addition of the critical amount of water by any means known in the art, e.g., by the methods disclosed in Scartazzini et al., supra.

Vegetable-derived fatty acid esters of glycerol (glycerides) are the preferred solvents. Examples of vegetable-derived glycerides which may be used in the present invention are vegetable oils such as coconut oil, corn oil, cottonseed oil, palm kernel oil, palm oil, safflower oil, sesame oil, peanut oil and soybean oil. Preferred vegetable oils are sesame oil, peanut oil and soybean oil.

The preferred glycerides are triglycerides in which the fatty acids have from 8–10 carbon atoms. Such triglycerides are referred to as medium chain triglycerides (MCT's). Especially preferred is an MCT of fractionated coconut oil fatty acids $C_8$–$C_{10}$ which contains 50–65% caprylic acid (C 8.0) and 30–45% capric acid (C 10.0), and no more than 2% caproic acid (C 6.0) and 3% lauric acid (C 12.0). Such an MCT is manufactured by Dynamit Nobel under the name MIGLYOL 812, and may be obtained from Kay-Fries, Inc., Montvale, N.J.

The weight ratio of lecithin to organic solvent in the compositions of the invention is not critical, so long as the composition is capable of forming a lecithin gel. The preferred weight ratio of lecithin to solvent is within the range from about 0.1 to about 2.0, with a weight ratio of about 0.3 being especially preferred.

The compositions of the invention may also include substances which act to stabilize the active ingredient. These stabilizing substances will differ depending on the particular active ingredient that will be incorporated into the composition. Examples of conventional protein and polypeptide stabilizers are human serum albumin (HSA), α-tocopherol and disodium ethylene diamine tetra acetic acid ("disodium EDTA").

The compositions of the invention may also include preservatives which retard the growth of bacteria in the composition during storage. Examples of conventional preservatives are methylparaben and propylparben.

In a preferred embodiment of the invention, the compositions of the invention further comprise excipients which act to modify the properties of the lecithin gel which forms in vivo after subcutaneous or intramuscular administration of a composition of the invention. Such excipients include:

(1) Osmotic Agents

Osmotic agents increase the rate of water sorption into the lecithin gel and provide an increase in the rate of release of the active ingredient which is relatively uniform over the life of the gel. Any conventional osmotic agents may be used in accordance with the invention. Preferred osmotic agents are mannitol, dextrose, and sodium chloride.

(2) Hydrophobic Agents

Hydrophobic agents reduce the rate of elimination of the lecithin gel from the injection site and decrease the rate of release of the active ingredient. Any conventional hydrophobic agents may be used in accordance with the invention. Preferred hydrophobic agents are cholesterol and cholesterol derivatives such as cholesterol sulfate, cholesterol acetate and cholesterol hemisuccinate; and (3) Surface Active Agents Surface active agents increase the rate of elimination of the lecithin gel from the injection site and provide an initially high rate of release of the active ingredient. Any conventional surface active agents may be used in accordance with the invention. Preferred surface active agents are stearic acid, palmitic acid, $C_8$–$C_{26}$ carboxylic acids, and the salts of these acids. Other surface active agents include polyoxyethylene glycols (e.g., PLURONIC's) and polyoxyethylene sorbitan mono-oleates (e.g., POLYSORBATE's).

The above excipients (1)–(3) are preferably present individually in amounts of 0.1–1.0 parts by weight to 1 part by weight of solvent. However, the total amount of such excipients is preferably less than 1.5 parts by weight to 1 part by weight of solvent.

If the active ingredient is not readily dispersible in the lecithin/solvent mixture, the active ingredient may first be dissolved in a small amount of water or in a buffer solution which is known in the art to be appropriate for the particular active ingredient. Additionally, water or a buffer solution may be incorporated in a composition of the invention in order to start the process of gel formation, and thus increase the viscosity of the composition, prior to injection. In either of the above instances, the volume of water or buffer solution should be less than the amount that would cause the composition to separate into aqueous and non-aqueous phases, or would cause the viscosity of the composition to increase beyond the point where it could be administered by injection.

The ability of a lecithin gel formed in vivo from a composition of the invention to sustain the release of a biologically active compound may be determined by any conventional means. For example, the test composition containing the biologically active ingredient may be injected into suitable laboratory animals, e.g., rats. The blood level of the active ingredient in the laboratory animal is then observed over time.

The ability of a gel to sustain the release of an active ingredient can also be determined in vitro by measuring the release of the active ingredient upon immersion of the gel in successive test solutions. For example, the in vitro release rate of a compound of interest may be measured in pH 7.4 phosphate buffer. Triplicate samples of each gel (200 mg) are placed in the bottom of 1.5 mL microcentrifuge tubes with a syringe. Buffer solution (400 microliters) is then placed on the top of the gels. The centrifuge tubes are sealed and placed in an incubator shaker bath maintained at 37° C. and agitated at a rate of 120 rpm. At each timepoint, the buffer solution is removed and assayed using any means appropriate to detect the active ingredient. Fresh buffer is then added to the microcentrifuge tube containing the test samples, and the above steps are repeated until the level of the active ingredient is zero or insignificant.

In a preferred embodiment, the compositions of the invention for the sustained administration of interferon alfa comprise 1 part by weight of glyceride solvent, 0.1 to 2.0 parts by weight of a lecithin which is dispersed in said solvent and which contains more than about 90% phosphadityl choline, 0.1 to 1.0 parts by weight of one or more excipients wherein said excipients are selected from the group consisting of osmotic agents, hydrophobic agents and surface active agents and the total amount of said excipients does not exceed 1.5 parts by weight, and about 100 million International Units to about 300 million International Units of interferon alfa per gram of final composition.

The injectable compositions of Examples 1 (a)–(k), below, were prepared by the following method:

Non-Solvent Method (1) While sparging with nitrogen, heat lecithin solvent to 40° C.

(2) Add and disperse lecithin.

(3) Add and disperse excipients.

(4) Cool to 25° C.

(5) Homogenize for 10 minutes maintaining temperature below 40° C.

(6) Cool to 25° C., add active ingredient and blend until homogeneous.

The injectable compositions of the invention may also be prepared by the following method:

Solvent Method (1) While sparging with nitrogen, disperse lecithin solvent, lecithin and excipients in hexane.

(2) Add active ingredient and emulsify.

(3) While maintaining agitation, place mixing vessel under negative pressure until hexane is evaporated.

EXAMPLE 1

The following are examples of injectable compositions of the invention:

| Example 1 (a) | | |
|---|---|---|
| Interferon alfa-2a concentrated bulk sol. ($2.02 \times 10^{10}$ IU/ml) | 0.148 | mL |
| Ammonium acetate pH 5.0 buffer | 0.052 | mL |
| Lecithin (LIPOID S 100) | 6.0 | g |
| MCT (MIGLYOL 812) | 14.8 | g |
| Example 1 (b) | | |
| Interferon alfa-2a/mannitol lyophilizate ($5.4 \times 10^8$ IU/mg) | 0.5 | g |
| Lecithin (LIPOID S 100) | 3.0 | g |
| MCT (MIGLYOL 812) | 1.485 | g |
| Methylparaben | 0.009 | g |
| Propylparaben | 0.001 | g |
| dl-alpha tocopherol | 0.005 | g |
| Example 1 (c) | | |
| Interferon alfa-2a bulk sol. ($2.02 \times 10^8$ IU/ml) | 0.65 | mL |
| Ammonium acetate pH 5.0 buffer | 0.35 | mL |
| Lecithin (LIPOID S 100) | 6.0 | g |
| MCT (MIGLYOL 812) | 2.97 | g |
| Methylparaben | 0.018 | g |
| Propylparaben | 0.002 | g |
| dl-alpha tocopherol | 0.01 | g |
| Example 1 (d) | | |
| Interferon alfa-2a bulk sol. ($13.2 \times 10^8$ IU/ml) | 1 | mL |
| Cholesterol | 3.0 | g |
| Mannitol | 1.5 | g |
| Lecithin (LIPOID S 100) | 3.0 | g |
| MCT (MIGLYOL 812) | 4.0 | g |
| Example 1 (e) | | |
| Interferon alfa-2a bulk sol. ($11.3 \times 10^8$ IU/ml) | 0.9 | mL |
| Stearic Acid | 1.0 | g |
| Lecithin (LIPOID S 100) | 4.0 | g |
| MCT (MIGLYOL 812) | 4.0 | g |
| Human Serum Albumin (25% sol.) | 0.1 | mL |
| Example 1 (f) | | |
| Interferon alfa-2a bulk sol. ($16.6 \times 10^8$ IU/ml) | 4.86 | mL |
| Ammonium acetate pH 5.0 buffer | 1.03 | mL |
| Cholesterol | 9.0 | g |
| MCT (MIGLYOL 812) | 9.0 | g |
| Mannitol | 3.0 | g |
| Lecithin (LIPOID S 100) | 3.0 | g |
| Methylparaben | 0.016 | g |
| Propylparaben | 0.0018 | g |
| Example 1 (g) | | |
| Interferon alfa-2a bulk sol. ($16.6 \times 10^8$ IU/ml) | 4.86 | mL |
| pH 5.0 ammonium acetate buffer | 1.03 | mL |
| Stearic Acid | 9.0 | g |
| MCT (MIGLYOL 812) | 9.0 | g |
| Mannitol | 3.0 | g |
| Lecithin (LIPOID S 100) | 3.0 | g |
| Methylparaben | 0.016 | g |
| Propylparaben | 0.0018 | g |
| Example 1 (h) | | |
| Interferon alfa-2a bulk sol. ($16.6 \times 10^8$ IU/ml) | 4.86 | mL |
| pH 5.0 ammonium acetate buffer | 1.03 | mL |
| Cholesterol | 4.5 | g |
| Stearic Acid | 4.5 | g |
| MCT (MIGLYOL 812) | 9.0 | g |
| Mannitol | 3.0 | g |
| Lecithin (LIPOID S 100) | 3.0 | g |
| Methylparaben | 0.016 | g |
| Propylparaben | 0.0018 | g |
| Example 1 (i) | | |
| GRF analog* | 0.003 | mg |
| pH 4.0 sodium acetate buffer | 3.957 | g |
| Cholesterol | 6.0 | g |
| MCT (MIGLYOL 812) | 6.0 | g |
| Mannitol | 2.0 | g |
| Lecithin LIPOID S 100 | 2.0 | g |
| Methylparaben | 0.004 | g |
| Propylparaben | 6.0 | g |
| Example 1 (j) | | |
| Interferon alfa-2a bulk sol. ($16.6 \times 10^8$ IU/ml) | 0.453 | mL |
| Ammonium acetate pH 5.0 buffer | 2.0 | mL |
| Lecithin (LIPOID S 100) | 5.0 | g |
| MCT (MIGLYOL 812) | 10.0 | g |
| Cholesterol | 7.5 | g |
| Example 1 (k) | | |
| Interferon alfa-2a bulk sol. ($16.6 \times 10^8$ IU/ml) | 0.905 | mL |
| Ammonium acetate pH 5.0 buffer | 1.548 | mL |
| Lecithin (LIPOID S 100) | 5.0 | g |
| MCT (MIGLYOL 812) | 10.0 | g |
| Cholesterol | 7.5 | g |

*[His$^1$, Val$^2$, Gln$^8$, Ala$^{15}$, Leu$^{27}$]-GRF (1-32)-OH which contains the first 32 residues of natural GRF with the noted substitutions at residues 1, 2, 8, 15 and 27.

EXAMPLE 2

Determination of Duration of Release of IFN-alfa

Compositions of Examples 1(a)–1(h) containing IFN-alfa were each subcutaneously administered to three Sprague-Dawley rats. Additional rats were administered the IFN-alfa in a conventional vehicle (Normal Saline) for comparison.

Blood samples were drawn, and the plasma IFN-alfa levels were determined by an immunoradiometric assay (Celltech Ltd., Berkshire, England) or by an enzyme immunosorbant assay (EIA) by the procedure of Gallati et al., *J. Clin. Chem. Clin. Biochem.,* 20:907–914 (1982).

FIGS. 1–4 show the sustained release effect obtained in rats by administering the compositions of Examples 1(a)–1(h). The values are the average serum levels of interferon alfa-2a detected in three rats.

Figure 2:
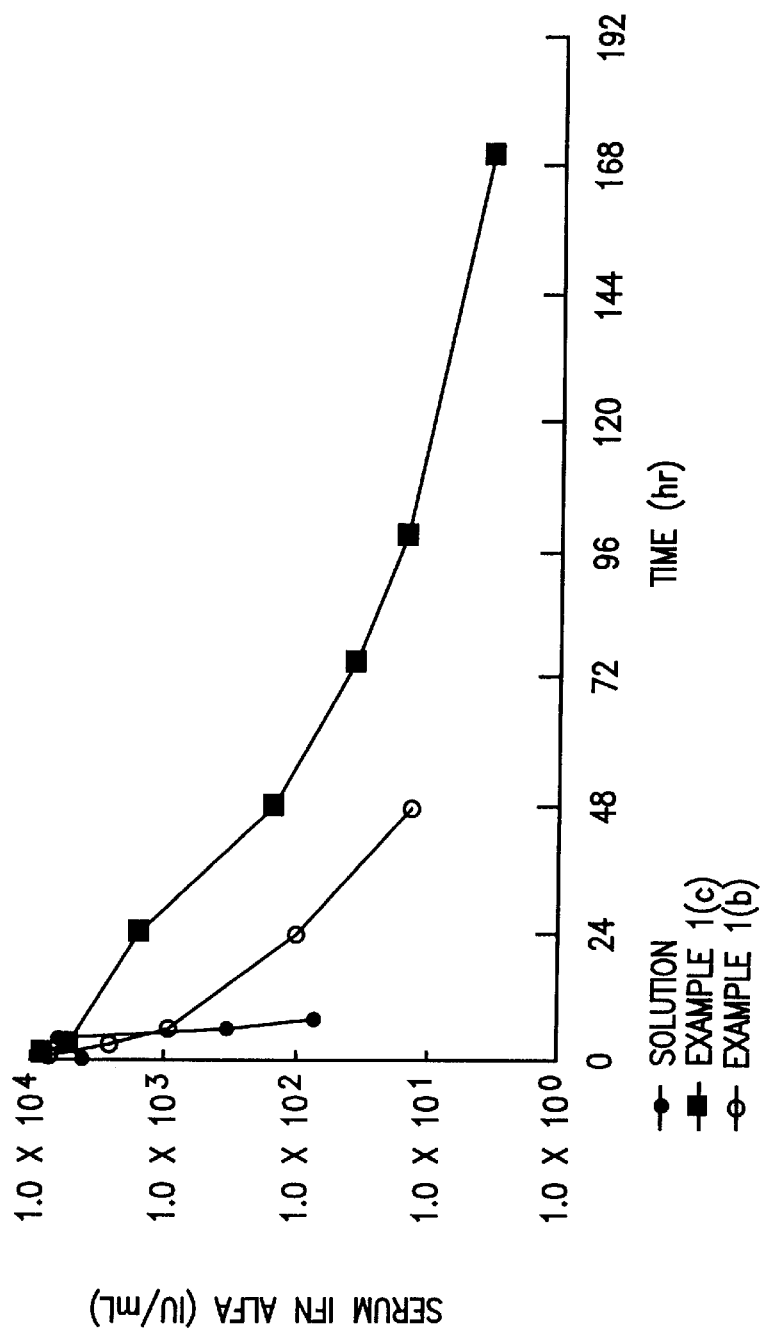

FIGS. 1 and 2 compare conventional solutions of interferon alfa-2a to compositions of the invention which contain no release-modifying excipients. FIG. 1 shows that when interferon-alfa 2a is administered in a conventional solution at a dose of 150 million units, the serum levels of interferon fell below detectable limits at 24 hours. However, FIG. 1 also demonstrates that the sustained release composition of Example 1(a) provided detectable serum levels for at least 96 hours. FIG. 2 demonstrates the sustained release obtained from the compositions of Examples 1(b) and 1(c) in comparison to a conventional solution at a dose of 54 million units per rat.

Figure 3:
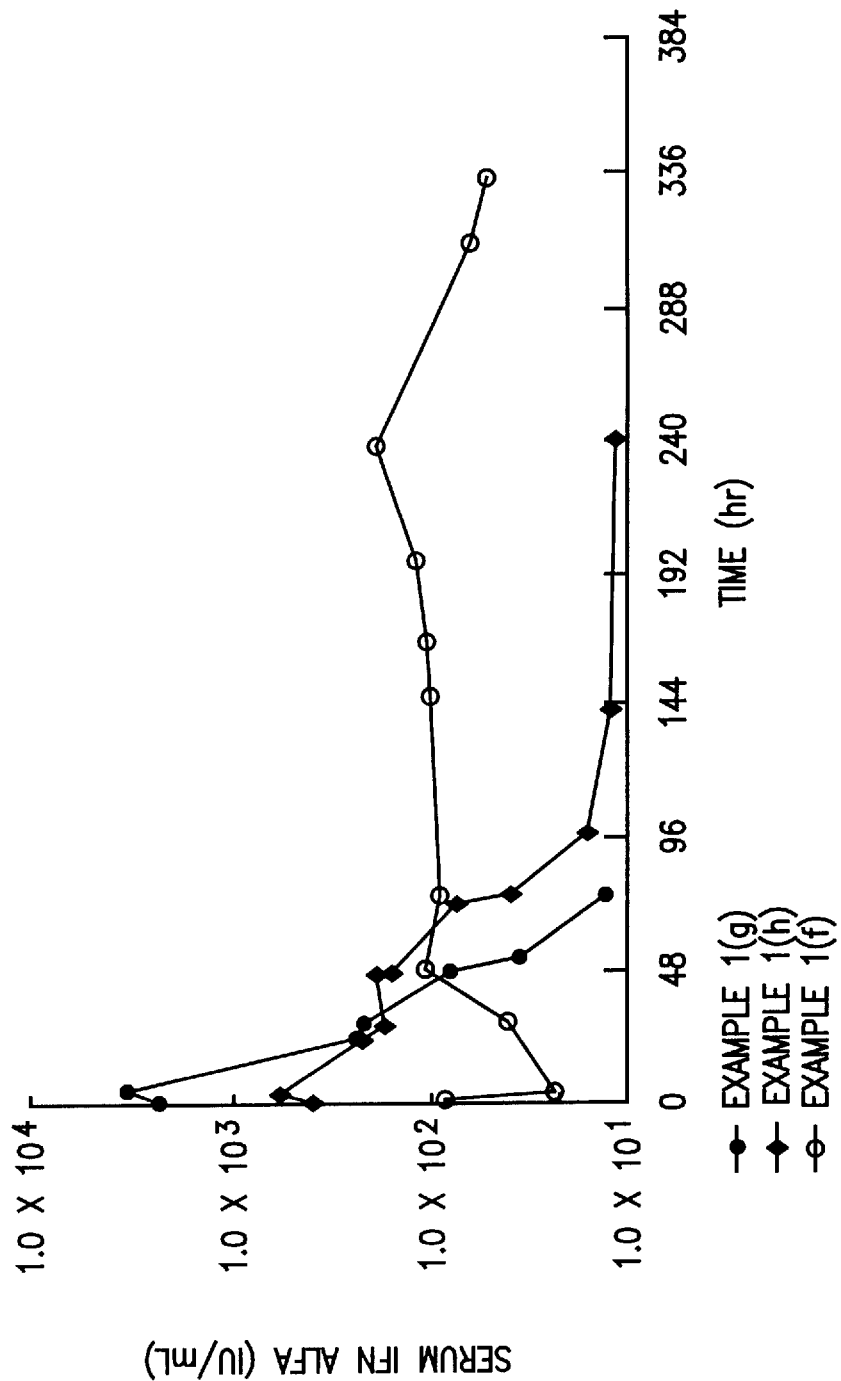
FIGS. 3 and 4 show the serum levels of interferon alfa-2a over time obtained from the administration in rats of interferon alfa-2a in compositions of the invention which contain release-modifying excipients.

FIG. 3 shows that the release of interferon in compositions of the invention may be altered by adding an osmotically active agent (mannitol) and adjusting the ratio of a hydrophobic additive (cholesterol) and a surface active agent (stearic acid) which aids in solubilizing the hydrophobic agent. The composition of Example 1(f) contains 30% cholesterol and detectable levels of interferon are observed for at least 336 hours. The composition of Example 1(h) is identical to 1(f) except, rather than containing 30% cholesterol, it contains 14% cholesterol and 15% stearic acid. The release period of interferon alfa-2a lasted approximately 240 hours from this composition. The composition of Example 1(g), containing no cholesterol and 30% stearic acid, had the shortest period of release, lasting approximately 72 hours. FIG. 3 demonstrates that the release of interferon in the compositions of the invention can be controlled by adding additional excipients.

Figure 4:
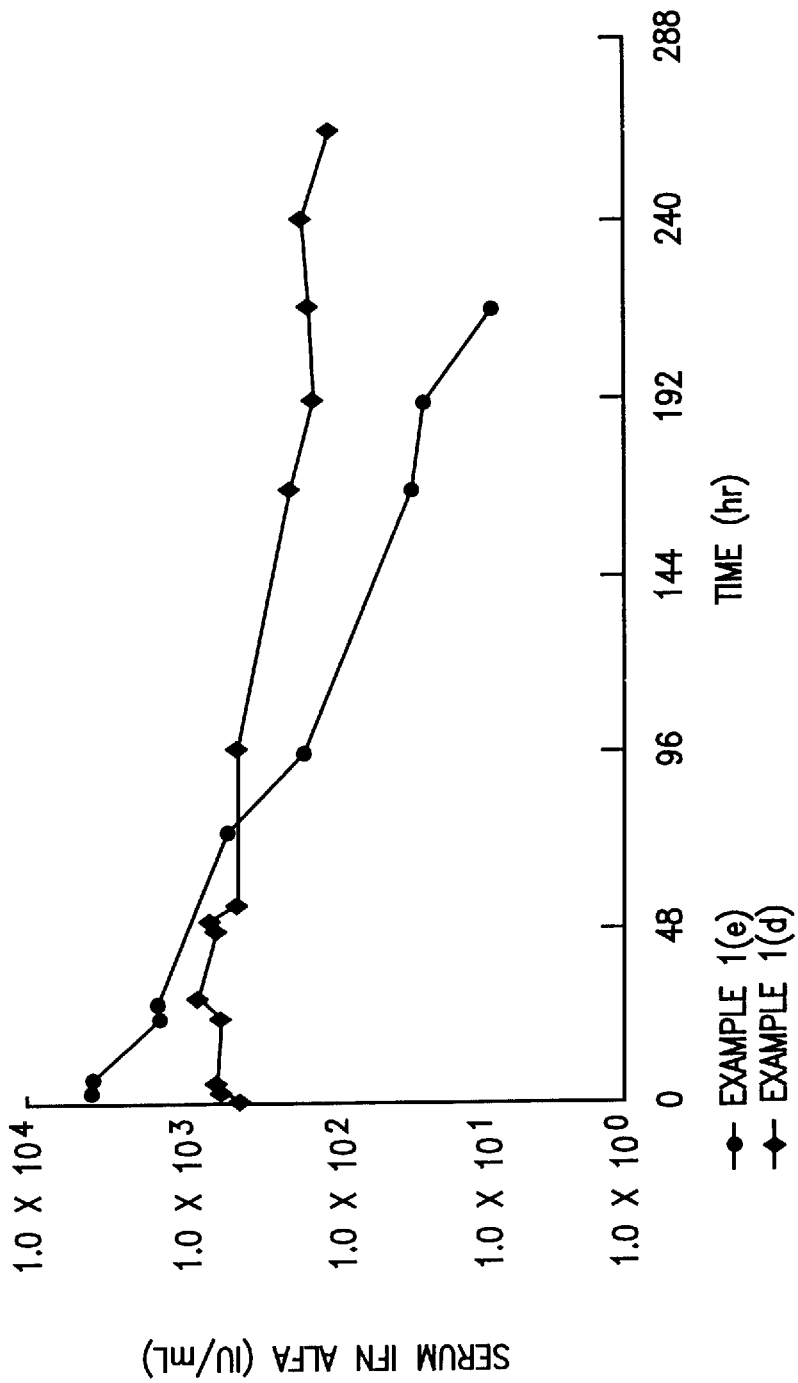

FIG. 4 shows the release periods obtained with compositions of Examples 1(d) and 1(e), further demonstrating the versalitity of the invention.

The results in FIGS. 1–4 demonstrate that the compositions of the invention significantly increase the time during which IFN-alfa is present in the blood of the test animal in comparison to conventional IFN-alfa solutions. With the conventional IFN-alfa solutions, the blood level of IFN-alfa returned to zero within 24 hours of administration. With the compositions of the invention containing IFN-alfa, the blood level of IFN-alfa did not return to zero until from 47.5 to greater than 300 hours after administration, depending upon the formulation of the composition.

EXAMPLE 3

Determination of Duration of Release of a GRF Analog

Figure 5:
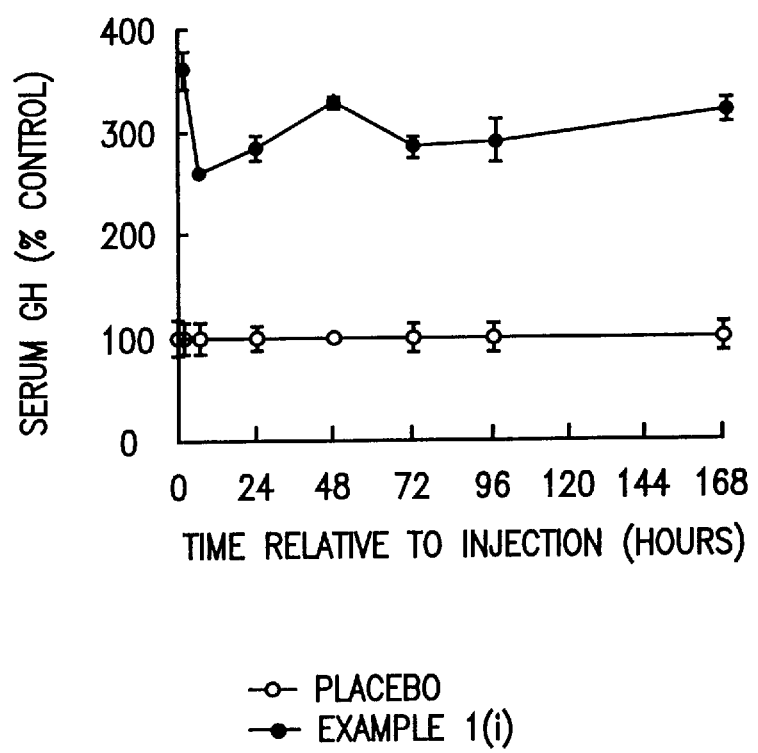
FIG. 5 shows the serum level of growth hormone which was induced in mice over a period of 168 hours from the injection of a growth hormone releasing factor analog in a composition of the invention which contains release-modifying excipients.

The composition of Example 1(i) containing a GRF analog was subcutaneously administered to C57/BL6 mice. Over a period of 7 days, blood samples were drawn at regular intervals and assayed for the presence of growth hormone. The results are shown in FIG. 5 which shows the blood level of growth hormone which was induced over a period of 168 hours from the injection of the formulation of Example 1(i). There were five mice in each test group (drug and placebo). The increased presence of growth hormone in the mice which were injected with the formulation of Example 1(i) demonstrates the ability of the compositions of the invention to sustain the release of a GRF analog in vivo.

EXAMPLE 4

Determination of Anti-Tumor Activity of Compositions Containing IFN alfa-2a

Figure 6:
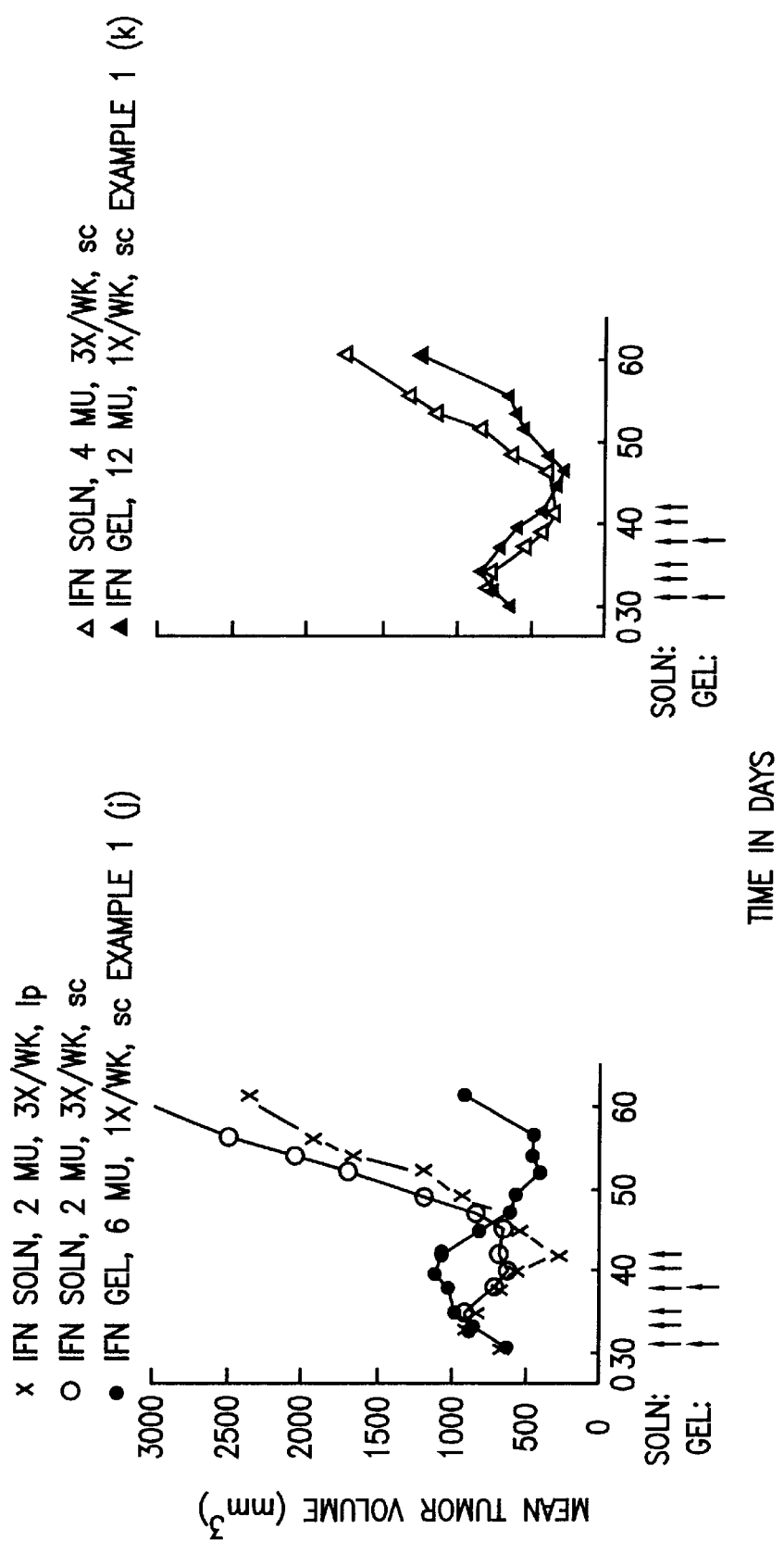
FIG. 6 shows the anti-tumor effect over time obtained from the administration in mice containing implanted tumors of interferon alfa-2a in conventional solutions and in compositions of the invention which contain release-modifying excipients.

Human lymphoma cells were implanted in athymic nude mice and allowed to grow. The mice were administered IFN alfa-2a in a conventional vehicle three times per week or in a composition of the invention (compositions of Examples 1(j) and 1(k)) once per week. The total IFN alfa-2a administered per week was the same in both groups. FIG. 6 shows the effects of the conventional IFN-alfa compositions and compositions of Examples 1(j) and 1(k) on the size of the implanted tumors over time.

The results in FIG. 6 demonstrate that the compositions of the invention, when administered once weekly, inhibit the growth of implanted tumors as effectively as conventional compositions administered 3 times per week.

I claim:

1. A method of forming a lecithin gel in vivo for the sustained release of a biologically active compound comprising subcutaneously or intramuscularly injecting into a host a pharmaceutical solution or suspension comprising:
    1) an organic solvent which is pharmaceutically acceptable for subcutaneous or intramuscular injection and which is not substantially soluble in water;
    2) a therapeutically effective amount of said biologically active compound which is dispersed in said solvent;
    3) about 0.1 to about 2.0 parts by weight to 1 part by weight of said solvent of a lecithin which is dispersed in said solvent.

2. The method of claim 1 wherein said composition further comprises excipients dispersed in said solvent, wherein said excipients are selected from the group consisting of osmotic agents, hydrophobic agents, and surface active agents, either alone or in combination.

3. The method of claim 2 wherein the individual excipients are present in an amount from about 0.1 to about 1.0 parts by weight per 1 part by weight of solvent, and the total amount of excipients is less than about 1.5 parts by weight per 1 part by weight of solvent.

4. The method of claim 3 wherein said solvent is a vegetable-derived glyceride or mixture of glycerides.

5. The method of claim 4 wherein said solvent is a medium chain triglyceride or mixture of medium chain triglycerides.

6. The method of claim 5 wherein the lecithin contains more than about 90% phosphadityl choline.

7. The method of claim 6 wherein the osmotic agents are selected from the group consisting of mannitol, dextrose and sodium chloride.

8. The method of claim 7 wherein the hydrophobic agents are selected from the group consisting of cholesterol, cholesterol sulfate, cholesterol acetate and cholesterol hemisuccinate.

9. The method of claim 8 wherein the surface active agents are selected from the group consisting of stearic acid, palmitic acid, $C_8$–$C_{26}$ carboxylic acids, and the salts of these acids, polyoxyethylene glycols and polyoxyethylene sorbitan mono-oleates.

10. The method of claim 9 wherein the excipients in the composition comprise cholesterol, mannitol, and stearic acid.

11. The method of claim 9 wherein the excipients in the composition comprise stearic acid.

12. The method of claim 11 wherein the excipients in the composition further comprise mannitol.

13. The method of claim 9 wherein the biologically active compound is interferon alfa.

14. The method of claim 9 wherein the biologically active compound is growth hormone releasing factor or an analog thereof having growth hormone releasing factor activity.

15. A method for the sustained treatment of a patient with a biologically active compound in the form of a gel for sustained release comprising subcutaneously or intramuscularly injecting into the patient a pharmaceutical solution or suspension comprising:

1) an organic solvent which is pharmaceutically acceptable for subcutaneous or intramuscular injection and which is not substantially soluble in water;

2) a therapeutically effective amount of said biologically active compound which is dispersed in said solvent;

3) about 0.1 to about 2.0 parts by weight to 1 part by weight of said solvent of a lecithin which is dispersed in said solvent.

16. The method of claim 15 wherein said composition further comprises excipients dispersed in said solvent, wherein said excipients are selected from the group consisting of osmotic agents, hydrophobic agents, and surface active agents, either along or in combination.

17. The method of claim 16 wherein the individual excipients are present in an amount from about 0.1 to about 1.0 parts by weight per 1 part by weight of solvent, and the total amount of excipients is less than about 1.5 parts by weight per 1 part by weight of solvent.

18. The method of claim 17 wherein the solvent is a vegetable-derived glyceride or mixture of glycerides.

19. The method of claim 18 herein the solvent is a medium chain triglyceride or mixture of medium chain triglycerides.

20. The method of claim 19 wherein the lecithin contains more than about 90% phosphadityl choline.

21. The method of claim 20 wherein the osmotic agents are selected form the group consisting of mannitol, dextrose and sodium chloride.

22. The method of claim 21 wherein the hydrophobic agents are selected from the group consisting of cholesterol, cholesterol sulfate, cholesterol acetate and cholesterol hemisuccinate.

23. The method of claim 22 wherein the surface active agents are selected from the group consisting of stearic acid, palmitic acid, $C_8$–$C_{26}$ carboxylic acids, and the salts of these acids, polyoxyethylene glycols and polyoxyethylene sorbitan mono-oleates.

24. The method of claim 23 wherein the excipients in the composition comprise cholesterol, mannitol, and stearic acid.

25. The method of claim 23 wherein the excipients in the composition comprise stearic acid.

26. The method of claim 25 wherein the excipients in the composition further comprise mannitol.

27. The method of claim 23 wherein the biologically active protein is interferon alfa.

28. The method of claim 23 wherein the biologically active polypeptide is growth hormone releasing factor or an analog thereof having growth hormone releasing factor activity.

* * * * *